US009863945B2

(12) United States Patent
Ito (10) Patent No.: US 9,863,945 B2
(45) Date of Patent: Jan. 9, 2018

(54) IMMUNOCHROMATOGRAPHY DETECTION METHOD (71) Applicant: TANAKA KIKINZOKU KOGYO K.K., Tokyo (JP)

(72) Inventor: Daisuke Ito, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 258 days.

(21) Appl. No.: 14/386,653

(22) PCT Filed: Mar. 13, 2013

(86) PCT No.: PCT/JP2013/057094
§ 371 (c)(1),
(2) Date: Jan. 15, 2015

(87) PCT Pub. No.: WO2013/141122
PCT Pub. Date: Sep. 26, 2013

(65) Prior Publication Data
US 2015/0118675 A1    Apr. 30, 2015

(30) Foreign Application Priority Data

Mar. 22, 2012 (JP) .................. 2012-066409

(51) Int. Cl.
G01N 33/558    (2006.01)
G01N 33/538    (2006.01)
G01N 33/569    (2006.01)

(52) U.S. Cl.
CPC ......... G01N 33/558 (2013.01); G01N 33/538 (2013.01); G01N 33/56983 (2013.01)

(58) Field of Classification Search
CPC ... G01N 33/558; G01N 33/528; G01N 33/543
See application file for complete search history.

(56) References Cited

U.S. PATENT DOCUMENTS

| 5,972,720 A | 10/1999 | Nichtl et al. |
| 7,935,541 B2* | 5/2011 | Chiku .................. G01N 33/558 435/7.1 |
| 2003/0180967 A1 | 9/2003 | Shigetoh |
| 2009/0203153 A1* | 8/2009 | Yang .................. C08G 65/3342 436/525 |
| 2009/0203155 A1 | 8/2009 | Chiku |
| 2011/0104709 A1* | 5/2011 | Yoshimizu ....... G01N 33/54393 435/7.1 |

FOREIGN PATENT DOCUMENTS

| CN | 1482460 A | 3/2004 |
| CN | 1800853 A | 7/2006 |
| CN | 102077091 A | 5/2011 |
| CN | 102246036 A | 11/2011 |
| EP | 0811846 A2 | 12/1997 |
| JP | 09-080051 A | 3/1997 |
| JP | 10-73594 A | 3/1998 |
| JP | 2003-344397 A | 12/2003 |
| JP | 2009-180580 A | 8/2009 |
| JP | 2009-192223 A | 8/2009 |
| JP | 2009-192228 A | 8/2009 |
| JP | 2011-196996 A | 10/2011 |

OTHER PUBLICATIONS

Sigma-Aldrich (retrieved on Sep. 29, 2016).*
Office Action for Taiwan Patent Application No. 102110307, dated Nov. 20, 2015.
International Search Report PCT/JP2013/057094, dated Jun. 4, 2013.
Office Action for Chinese Patent Application No. 2013800154126—Notification of the First Office Action, dated Jun. 3, 2015.

* cited by examiner

Primary Examiner — Tracy Vivlemore
Assistant Examiner — Nam P Nguyen
(74) Attorney, Agent, or Firm — Orrick, Herrington & Sutcliffe LLP; Joseph A. Calvaruso (57) ABSTRACT The present invention provides an immunochromatography detection method capable of suppressing non-specific reactions. The present invention relates to an immunochromatography detection method including: a step of adding an analyte dilution solution containing an analyte to a chromatography medium; a step of recognizing a detection target by a labeling substance modified with gold nanoparticles, which is dry-retained at a labeling substance retaining part; a step of developing a composite of the labeling substance and the detection target as a mobile phase; and a step of detecting the detection target in the developed mobile phase at a judgment part, wherein the labeling substance is protected with a polyalkylene glycol having one or more mercapto groups and/or a derivative thereof and then dry-retained together with arginine and casein at the labeling substance retaining part.

8 Claims, 1 Drawing Sheet

IMMUNOCHROMATOGRAPHY DETECTION METHOD

TECHNICAL FIELD

The present invention relates to a high-performance and high-sensitivity immunochromatography detection method which suppresses nonspecific reactions. Moreover, the present invention relates to a detection kit capable of testing/measuring a detection target in a sample promptly, simply, and precisely with suppressing nonspecific reactions.

More specifically, the present invention relates to a method for testing a detection target in a sample promptly, simply, and precisely with protecting and stabilizing a labeling substance labeled with metal nanoparticles for detecting a detection target (substance to be detected), i.e., a sensitized metal colloid in which metal colloidal particles are sensitized with a substance specifically binding to the detection target, against a drying treatment or in a dry state and suppressing nonspecific reactions.

BACKGROUND ART

In recent years, increased is the importance of a strip type immunoassay for immuno chromatography, which does not require pretreatment of a detection sample, as a simple and convenient in vitro diagnostic kit or a portable diagnostic device which detects an antigen in a sample liquid based on utilization of the specific reactivity of an antibody. In particular, a test kit for a pathogen such as a virus or a bacterium is a familiar immunochromatography device widely used in common hospitals or clinics.

The most simple structure of the immunochromatography device is a structure in which a sample addition site, a labeling substance retaining part, a judgment (detection) site, a porous support for immunochromatography, and a sample absorption site are mutually connected. The labeling substance retaining part has been produced by treating with a protective stabilizing solution a labeling substance (hereinafter also referred to as conjugate) labeled with metal nanoparticles for detecting a detection target, subsequently impregnating or coating the porous support for immunochromatography with the substance, and then performing air drying, vacuum drying, freeze drying, or the like.

As the protective stabilizing solution, hitherto, those containing a protein such as bovine serum albumin (BSA) as a protective stabilizing agent have been known but there is a problem that they cannot be maintained stably in a dry state over a long period of time, so that further improvement and investigation have been carried out. For example, those containing casein, a whey protein, or a casein decomposition product have been reported (see Patent Document 1).

Moreover, as protection and stabilization of a labeling antibody in various immunoassays, there has been known a technology of adding a biomolecule (e.g., antibody or the like) to a gold colloid and subsequently protecting and stabilizing the conjugate by incorporating polyethylene glycol substituted with a thiol and/or disulfide group therein (namely, aggregation of particles is minimized and a free surface capable of adsorption is saturated) (see Patent Document 2).

Furthermore, a protective stabilizing solution composed of 20 to 80% of a saccharide such as trehalose and a 0.5 to 2 mol/L buffer solution has been proposed as one capable of stably storing a solid-phase immunoreagent in a dry state for a long period of time (see Patent Document 3).

Moreover, in order to improve stabilization of a sensitized metal colloid-containing freeze-dried product, there is known a technology of incorporating one or more of trehalose, monoarginine glutamate, tryptophan, calcium chloride, and the like therein at the time of freezing and drying a sensitized metal colloid-containing solution (see Patent Document 4).

Furthermore, as an in vitro diagnostic drug composition having excellent storage stability of a protein, especially an enzyme stored in an aqueous solution and showing little decrease in diagnostic accuracy after three months of storage, it has been reported that a problem of inducing aggregation, hydrolysis, and the like of a protein in an aqueous solution can be solved by incorporating guanidine (a salt thereof) or arginine (a salt thereof or a derivative thereof) in addition thereto as a stabilizer (see Patent Document 5).

On the other hand, with regard to an immunochromatography device, it has been a conventionally recognized problem that background coloration (coloration of the part excluding the immobile-phase antibody at the judgment part), blank coloring (coloring of the immobilized phase in the case where a detection substance is absent), and a prozone phenomenon (false negative phenomenon in which a test substance is apparently observed as if it is present in a smaller amount when a large excess of the test substance is used as a sample) not only decrease the SN ratio at detection but also cause malfunction.

The background coloration is caused by hydrophobic bonding between a visualized mobile-phase antibody and a porous carrier, and the blank coloring is caused by an electrical interaction between a mobile-phase antibody having a negative electric charge and an immobile-phase carrier having a positive electric charge, which is also said as nonspecific coloring. Furthermore, the prozone phenomenon is considered to be attributable to a fact that excess test substance that has not been able to react with the labeling substance reacts with the judgment site and the labeling substance labeled with metal particles for detecting the test substance cannot react with the judgment site.

As countermeasures, a number of studies from various standpoints have been performed. For example, in an immunochromatography detection method which makes use of a developing solution containing a pH buffer and the like, various additives have been used for suppression of side reactions arising from biological affinity or for suppression of nonspecific reactions, and examples of such additives include, for promotion of an antigen-antibody reaction or for suppression of nonspecific reactions, proteins (e.g., bovine serum albumin, casein, gelatin, etc.), high molecular compounds (e.g., polyethylene glycol, dextran, methyl cellulose, polyvinylpyrrolidone, etc.), nonionic surfactants (e.g., Tween 20, Triton X-100, etc.), ionic surfactants or polyanions (e.g., dextran sulfate, heparin, polystyrenesulfonic acid, hyaluronic acid, chondroitin sulfate, etc.) or their salts, and the like (see Patent Document 6).

Moreover, there are known an immunochromatography analytic method in which a test substance is developed with a mobile phase containing a basic amino acid (e.g., arginine, lysin, or the like) or an amino sugar (e.g., glucosamine or the like) (see Patent Document 7) and a membrane assay method using an assay medium having an arginine concentration of 0.02 to 1.5M and pH of 7.0 to 9.5 and substantially containing no buffer other than arginine (see Patent Document 8).

Furthermore, as a countermeasure against the background coloration and the blank coloring and for suppressing the side reaction arising from biological affinity, suppressing nonspecific reactions, and stabilizing a conjugate such as the labeling antibody, there may be mentioned proteins (e.g., bovine serum albumin, gelatin, casein, whey proteins, materials containing a casein decomposed product, etc.), high molecular compounds (e.g., polyethylene glycol substituted with a thiol and/or disulfide group, etc.), basic amino acids (e.g., arginine, etc.), and the like.

However, even if the nonspecific reactions are suppressed, there arises a problem that detection sensitivity decreases, and thus the object is not yet satisfactory achieved, so that there is still a similar problem that the nonspecific reactions cannot be sufficiently suppressed.

CITATION LIST

Patent Documents

Patent Document 1: JP-A-9-80051
Patent Document 2: JP-A-10-73594
Patent Document 3: JP-A-2003-215127
Patent Document 4: JP-A-11-125635
Patent Document 5: JP-A-2011-196996
Patent Document 6: JP-A-2007-322310
Patent Document 7: JP-A-2001-289852
Patent Document 8: JP-A-2007-114049

SUMMARY OF THE INVENTION

Problems to be Solved by the Invention

As a result of performing experiments focusing on the above high molecular compounds (e.g., polyethylene glycol substituted with a thiol and/or disulfide group, etc.), the present inventors have observed that blank coloring and nonspecific reactions still take place at the time when a test substance in a sample is detected by an immunochromatography. Therefore, there still exists a problem of protecting and stabilizing a conjugate dry-retained at a labeling substance retaining part over a long period of time and sufficiently suppressing the nonspecific reactions to achieve an improvement in detection sensitivity.

The present invention provides a high-performance and high-sensitivity immunochromatography detection method that protects and stabilizes the labeling substance and suppresses the nonspecific reactions as compared with conventional technologies. Moreover, an object of the present invention is to provide an immunochromatography detection kit capable of performing a test promptly, simply, and highly precisely with protecting and stabilizing the labeling substance and suppressing the nonspecific reactions as compared with conventional technologies. Another object of the present invention is to provide an immunochromatography device capable of specifically reacting with a pathogen such as a virus or a bacterium to achieve a prompt and simple infection test of a pathogen.

Furthermore, an object of the present invention is to provide a detection kit capable of performing a test promptly, simply, and highly precisely with suppressing nonspecific reactions at the time when an analyte obtained by adjusting or diluting a sample with an analyte dilution solution to a concentration suitable for measurement is supplied to a sample addition part of the detection kit, the analyte is developed together with the labeling substance dry-retained at a labeling substance retaining part as a mobile phase, and a detection target in the developed mobile phase is detected at a judgment part.

An object of the present invention is to provide a detection kit capable of performing an infection test of a pathogen promptly, simply, and highly precisely by supplying one obtained by adjusting or diluting, for example, nasal discharge or phlegm with an analyte dilution solution to the sample addition part of the detection kit.

Moreover, still another object of the present invention is to provide a method for detecting a detection target in a sample by immunochromatography with suppressing nonspecific reactions.

Means for Solving the Problems

The present inventors have found that a labeling substance can be protected from a drying treatment and also be stably retained in a dry state over a long period of time by protecting the labeling substance with a polyalkylene glycol having one or more mercapto groups and/or a derivative thereof and subsequently dry-retaining the substance together with arginine and casein at the labeling substance retaining part at the time when a labeling substance retaining part is provided on an immunochromatography device, and they have been accomplished the present invention.

That is, the present invention is as follows.

1. An immunochromatography detection method comprising:
   a step of adding an analyte dilution solution containing an analyte into a chromatography medium;
   a step of recognizing a detection target by a labeling substance modified with gold nanoparticles, which is dry-retained at a labeling substance retaining part;
   a step of developing a composite of the labeling substance and the detection target as a mobile phase; and
   a step of detecting the detection target in the developed mobile phase at a judgment part,
   wherein the labeling substance is protected with a polyalkylene glycol having one or more mercapto groups and/or a derivative thereof, and subsequently dry-retained together with arginine and casein at the labeling substance retaining part.
2. The immunochromatography detection method described in 1 above, wherein the polyalkylene glycol having one or more mercapto groups and/or a derivative thereof is a polyethylene glycol having one or more mercapto groups and having a molecular weight of 1,000 to 30,000 and/or a derivative thereof.
3. The immunochromatography detection method described in 2 above, wherein the labeling substance is subjected to a protection treatment in a solution containing the polyethylene glycol having one or more mercapto groups and/or a derivative thereof and concentration of the polyethylene glycol and/or the derivative in the solution after the protection treatment of the labeling substance is from 0.0001 to 0.05% by mass.
4. The immunochromatography detection method described in any one of 1 to 3 above, wherein the above arginine and casein are dry-retained at the labeling substance retaining part with being contained in the labeling substance solution and impregnating the chromatography medium and, as a final concentration in the labeling substance solution before being moistened with the chromatography medium, concentration of arginine is from 0.01 to 2% by mass and concentration of casein is from 0.1 to 10% by mass.
5. The immunochromatography detection method described in any one of 1 to 4 above, wherein the gold nanoparticles are red gold nanoparticles having an average particle diameter of 30 to 100 nm or blue gold nanoparticles having an average particle diameter of 20 to 200 nm.
6. The immunochromatography detection method described in any one of 1 to 5 above, wherein the analyte is nasal discharge, a swab from nasal cavity, a swab from pharynx, or phlegm.
7. The immunochromatography detection method described in any one of 1 to 6 above, wherein guanidine is contained in the analyte dilution solution.
8. The immunochromatography detection method described in 7 above, wherein concentration of guanidine in the analyte dilution solution is from 1 to 200 mM.
9. An immunochromatography device comprised substantially and sequentially of a sample addition part, a labeling substance retaining part, a chromatography medium part, a detection part and an absorption part, wherein the labeling substance retaining part is provided between an edge part of the sample addition part and the detection part and the labeling substance is protected with a polyalkylene glycol having one or more mercapto groups and/or a derivative thereof and is dry-retained together with arginine and casein at the labeling substance retaining part.
10. A detection kit comprising an immunochromatography device comprised substantially and sequentially of a sample addition part, a labeling substance retaining part, a chromatography medium part, a detection part and an absorption part, wherein the labeling substance retaining part is provided between an edge part of the sample addition part and the detection part and the labeling substance is protected with a polyalkylene glycol having one or more mercapto groups and/or a derivative thereof and is dry-retained together with arginine and casein at the labeling substance retaining part.

Effect of the Invention

In the immunochromatography detection method of the present invention, at the time when a labeling substance retaining part is provided on an immunochromatography device, a labeling substance labeled with metal nanoparticles for detecting a detection target is protected with a polyalkylene glycol having one or more mercapto groups and/or a derivative thereof and dry-retained together with arginine and casein at the labeling substance retaining part. Thereby, the sensitized metal colloid in which the metal colloid particles are sensitized with a substance specifically binding to the detection target can be protected from a drying treatment and also stably retained in a dry state over a long period of time at the labeling substance retaining part.

Therefore, according to the immunochromatography detection method of the present invention, at the time of detecting a detection target (e.g., antigen or the like) in a sample, nonspecific reactions can be remarkably suppressed owing to the combined effects of three factors: the polyalkylene glycol having one or more mercapto groups and/or a derivative thereof and arginine and casein which act cooperatively, although details of a principle of the stabilization or the suppressing mechanism of the nonspecific reactions are unknown. Furthermore, no decrease in sensitivity is observed and precise judgment of results is possible.

For example, at the time of detecting a virus or the like in a swab from pharynx used as an analyte, no decrease in sensitivity is observed and it is possible to precisely judge the results of a test for the presence of infection and the like.

The test kit for immunochromatography of the present invention is effective for a test for the presence of a pathogen and particularly, it is possible to perform a prompt and precise test for the presence of a particular virus, appropriate curative measures can be taken, so that the kit is preferably used at medical sites.

EMBODIMENTS FOR CARRYING OUT THE INVENTION

The following will describe the present invention in detail.

The present invention relates to an immunochromatography detection method comprising: a step of adding an analyte dilution solution into a chromatography medium; a step of recognizing the detection target by a labeling substance modified with gold nanoparticles, which is dry-retained at a labeling substance retaining part; a step of developing a composite of the labeling substance and the detection target as a mobile phase; and a step of detecting the detection target in the developed mobile phase at a judgment part, wherein the labeling substance is protected with a polyalkylene glycol having one or more mercapto groups and/or a derivative thereof, and subsequently dry-retained together with arginine and casein at the labeling substance retaining part.

Since the labeling substance is protected with a polyalkylene glycol having one or more mercapto groups and/or a derivative thereof, and subsequently dry-retained together with arginine and casein at the labeling substance retaining part, the sensitized metal colloid in which the metal colloid particles are sensitized with a substance (e.g., a biomolecule such as an antibody, an antigen, an enzyme, or a peptide) specifically binding to the detection target can be stably protected from a drying treatment and also stably retained in a dry state over a long period of time at the labeling substance retaining part.

Although the mechanism is unknown, it is assumed that three substances of the polyalkylene glycol having one or more mercapto groups and/or a derivative thereof, and arginine and casein play an action that they cover and saturate a free surface of metal particles in the labeling substance through combined adsorption with cooperative action and thereby the possibility of adsorption which may induce nonspecific reactions is noticeably dissipated and the aggregation of the metal particles is retained at minimum.

Moreover, there is assumed an action that hydrophobic bonding between the mobile-phase antibody and the porous carrier and electrical interaction between the mobile-phase antibody and the immobile-phase carrier are highly canceled by interaction among arginine, the polyalkylene glycol having one or more mercapto groups and/or a derivative thereof, and casein.

Furthermore, it is assumed that the stabilization of the detection target and the labeled detection reagent and the stabilization of the composite obtained by the reaction of the detection target with the labeling antibody are achieved by synergism among the polyalkylene glycol having one or more mercapto groups and/or a derivative thereof, arginine, and casein and simultaneously they plays an action to smoothen their migration as a mobile phase.

By these actions, the immunochromatography detection method of the present invention can specifically detect/measure the detection target in the sample highly sensitively and promptly with high precision with extremely remarkably suppressing nonspecific reactions.

The polyalkylene glycol having one or more mercapto groups and/or a derivative thereof for use in the present invention is preferably a polyalkylene glycol having a molecular weight of preferably 1,000 to 30,000, more preferably 2,000 to 20,000 and having one or more mercapto groups and/or a derivative thereof.

Examples of the portion having one or more mercapto groups include monomercapto or dimercapto. Examples of the case of having a branched structure include trimercapto and tetramercapto.

Examples of the polyalkylene glycol and/or a derivative thereof include homopolymers such as polyethylene glycol (referred to as "PEG"), polypropylene glycol (referred to as "PPG"), and polybutylene glycol (referred to as "PBG") and random copolymers composed of arbitrary constitutional ratio of an ethylene glycol (referred to as "EG") segment, a propylene glycol (referred to as "PG") segment and a butylene glycol (referred to as "BG") segment, for example, those in which EG, PG and BG are mixed or block copolymers in which PEG, PPG and PBG blocks are mixed.

For example, there may be mentioned polymers arbitrarily containing EG, PG, BG randomly or as blocks, such as HS-PEG, HS-PEG-SH, HS-PPG, HS-PPG-SHSH-PBG, HS-PBG-HS, HS-PEG-PPG, HS-PEG-PPG-HS, HS-PEG-PBG-HS, and HS-PEG-PPG-PBG-HS.

A polymer particularly useful for carrying out the present invention belonging to the category of the portion of the polyalkylene glycol and/or a derivative thereof is polyethylene glycol (PEG). With regard to a molecular weight thereof, those having a molecular weight ranging from 1,000 to 30,000, as examples of specific molecular weight, those having an arbitrary molecular weight such as 1,500, 5,000, 8,000, 15,000, 18,000, or 25,000 may be used. Actually, since it is difficult to obtain one having a molecular weight of an accurate numerical value thereof, it is sufficient to obtain and use one having a molecular weight around the numerical value.

In any event, an essential requirement is to belong to the category of the polyalkylene glycol having one or more mercapto groups and/or a derivative thereof. The polyalkylene glycol having one or more mercapto groups and/or a derivative thereof can be used even as a mixture thereof.

The polyethylene glycol (PEG) having a molecular weight of 1,000 to 30,000 and having one or more mercapto groups and/or a derivative thereof to be most suitably used for the protection of the labeling substance for immunochromatography of the present invention is represented by the general formula:

X—(CH$_2$CH$_2$O)$n$-CH$_2$CH$_2$—SH wherein X represents HS—, HO— which may be protected, or alkyl-O— and n represents an integer of 15 to 540. As the derivative, there may be mentioned derivatives having protective groups of OH and SH that are end groups. For example, in the case of OH, there may be mentioned protective groups frequently used in the field of peptide synthesis, a p-toluenesulfonyl group, a carbonyl group, and the like. An alkyl group is preferred and particularly a methyl group is preferred.

As specific polyethylene glycol having one or more mercapto groups and/or a derivative thereof, there may be, for example, mentioned monomercaptopolyethylene glycol and dimercaptopolyethylene glycol. As the case of having a branched structure, there may be, for example, mentioned trimercaptopolyethylene glycol and/or a derivative thereof.

As the polyethylene glycol (PEG) having one or more mercapto groups and/or a derivative thereof, those having a molecular weight (a molecular weight of 1,000 to 30,000) commercially available are available and usable.

A particularly preferable molecular weight of the polyethylene glycol (PEG) having one or more mercapto groups and/or a derivative thereof is from 2,000 to 20,000. Examples thereof include methoxy-PEG-thiol 2000, thiol-PEG-thiol 3400, methoxy-PEG-thiol 5000, methoxy-PEG-thiol 20000, and the like.

By controlling the molecular weight of the polyethylene glycol (PEG) having one or more mercapto groups and/or a derivative thereof to 2,000 or more, the stability against drying and the protective function can be prevented from being insufficiently exhibited even when PEG modification of the labeling substance is sufficient. Moreover, the suppression of nonspecific reactions can be improved.

Furthermore, by controlling the molecular weight of the polyethylene glycol (PEG) having one or more mercapto groups and/or a derivative thereof to 20,000 or less, the PEG modification of the labeling substance becomes homogeneous and sufficient. As a result, the stability against drying and the protective function can be uniformly and sufficiently exhibited. In addition, the suppression of nonspecific reactions can be improved.

When the molecular weight falls within the range of 1,000 to 30,000, not only the polyethylene glycol can be obtained as relatively high pure one but also the PEG modification of the labeling substance is sufficiently performed, the stability against drying and the protective function can be uniformly and sufficiently exhibited, and the suppression of nonspecific reactions is sufficiently performed, so that the case is preferred.

The polyalkylene glycol having a molecular weight of 1,000 to 30,000 and having one or more mercapto groups and/or a derivative thereof is preferably used but, in some cases, there can be used a polymer blend obtained by blending two kinds of mercapto group-containing polyalkylene glycols or derivatives thereof different in molecular weight in an arbitrary ratio, such as PEG having a molecular weight of 3,000 and PEG having a molecular weight of 8,000.

Similarly, in consideration from the viewpoint of the mercapto group, there may be mentioned a polymer blend obtained by blending a polyalkylene glycol having one mercapto group or a derivative thereof and a polyalkylene glycol having two mercapto groups or a derivative thereof in an arbitrary ratio, such as a mixture of "HS-PEG and HS-PEG-SH".

Furthermore, there may be mentioned a polymer blend of about 20 to 99% by mass of a polyalkylene glycol having one or more mercapto groups or a derivative thereof and about 1 to 80% by mass of a polyalkylene glycol having no mercapto group or a derivative thereof, such as a mixture of "HS-PEG and PEG". In the case of this polymer blend, care must be taken in adjusting the blending amount thereof so as not to lower the function of the polyalkylene glycol having one or more mercapto groups.

As an example of two kinds of mercapto group-containing polyalkylene glycols and/or derivatives thereof different in molecular weight in the polymer blend, it is possible to use a mixture of thiol-PEG-thiol 3400 and methoxy-PEG-thiol 5000.

As a concentration of the polyalkylene glycol having one or more mercapto groups and/or a derivative thereof, especially representative polyethylene glycol having one or more mercapto groups and/or a derivative thereof in the case of the use in the labeling substance in which a reagent component (e.g., antibody or the like) that specifically reacts with the detection target is modified with gold nanoparticles, the concentration of the polyethylene glycol having one or more mercapto groups and/or a derivative thereof in a solution after the labeling substance is subjected to a protection treatment with the polyethylene glycol having one or more mercapto groups and/or a derivative thereof is preferably from 0.0001 to 0.05% by mass, more preferably from 0.0005 to 0.01% by mass. For example, methoxy-PEG-thiol having a molecular weight of 5,000 and having a concentration of about 0.001% by mass in water can be used.

By controlling the concentration of the polyalkylene glycol having one or more mercapto groups and/or a derivative thereof in the solution to 0.0001% by mass or more, the stability against drying and the protective function become sufficient and the blank coloring and the nonspecific reactions can be suppressed, so that correct judgment can be performed. By controlling the concentration to 0.05% by mass or less, aggregation of the labeling substance particles are suppressed and the concentration becomes a necessary and sufficient concentration, so that the case is economical.

Arginine for use in the present invention is a naturally existing amino acid that is also called 5-guanidino-2-aminopentanoic acid. As arginine, L-arginine ($C_6H_{14}N_4O_2$) is preferred.

Arginine is preferably dry-retained at the labeling substance retaining part by incorporating it into a labeling substance solution and impregnating a chromatography medium with it. A final concentration of arginine in the labeling substance solution before impregnating the chromatography medium with it is preferably from 0.01 to 2% by mass, more preferably from 0.02 to 0.5% by mass in the solution. For example, a 0.1% by mass aqueous L-arginine solution is preferably used.

By controlling the final concentration of arginine to 0.01% by mass or more, the stability against drying and the protective function become sufficient and the blank coloring and the nonspecific reactions can be suppressed, so that correct judgment can be performed. By controlling the concentration to 2% by mass or less, the concentration becomes a necessary and sufficient concentration, so that the case is economical.

Casein is one kind of naturally existing phosphoproteins contained in milk and cheese. Examples of casein for use in the present invention include casein itself and skim milk containing casein as a main component.

Casein is preferably dry-retained at the labeling substance retaining part by incorporating it into a labeling substance solution and impregnating a chromatography medium with it. A final concentration of casein in the labeling substance solution before impregnating the chromatography medium with it is preferably from 0.1 to 10% by mass, more preferably from 0.2 to 5% by mass in the solution. For example, a buffer solution containing 1% by mass of casein is preferably used.

By controlling the final concentration of casein to 0.1% by mass or more, a sufficient action is exhibited. By controlling the concentration to 10% by mass or less, the concentration becomes a necessary and sufficient concentration, so that the case is economical.

It is preferable to mix an aqueous solution of arginine (abbreviated as "B") and an aqueous solution of casein (abbreviated as "C") into an aqueous solution of the labeling substance protected with the polyethylene glycol derivative having one or more mercapto groups with appropriately combining them so as to give such a concentration as mentioned above. The concentrations of B and C are preferably from 0.01 to 2% by mass and from 0.1 to 10% by mass, more preferably from 0.05 to 1% by mass and from 0.5 to 5% by mass, respectively.

In the present invention, it is preferable to incorporate guanidine or a salt thereof into the analyte dilution solution. The salt of guanidine may be an inorganic salt or an organic salt and examples thereof include hydrochloride, sulfate, phosphate, acetate, tartrate, malate, and citrate. Concentration of guanidine or a salt thereof is preferably from 1 to 200 mM, more preferably from 2 to 100 mM, further preferably from 5 to 50 mM in the analyte dilution solution.

As the analyte dilution solution, for example, a buffer solution containing 20 mM of guanidine hydrochloride is preferably used. By controlling the concentration of guanidine or a salt thereof in the analyte dilution solution to 1 mM or more, a sufficient action can be achieved. By controlling the concentration to 200 mM or less, the concentration becomes a necessary and sufficient concentration, so that the case is economical.

The gold nanoparticles for use in the present invention are preferably red gold nanoparticles having an average particle diameter of 30 to 100 nm and/or blue gold nanoparticles having an average particle diameter of 20 to 200 nm. Needless to say, particles of a noble metal such as platinum, silver, germanium, rhodium, or palladium, or nanoparticles of a metal such as titanium, iron, or zinc having an average particle diameter of preferably from about 10 to 250 nm, more preferably from about 35 to 120 nm can be also used.

Gold nanoparticles are most recommended in view of diagnostic accuracy but a mixture of metals such as gold and platinum containing gold as a main component can be also used. Furthermore, for a certain particular diagnosis, it is also possible to make such a contrivance that the metal nanoparticles are controlled to have the same shape, for example real sphere shape as far as possible or the particle diameter of individual particles is made even as far as possible.

The metal nanoparticles may be made in a dispersed state. For example, there may be mentioned sensitized metal colloid with an antibody or an antigen, sensitized gold colloid, sensitized platinum-gold colloid, sensitized gold-silver colloid, iron colloid, and the like. However, the gold colloid is recommended in view of easiness in handling, precision in measurement, and the like. The combined use of a colloidal gold-labeled sensitizer is also recommended for the purpose of improving the measurement sensitivity.

In the particular case where high sensitivity and high precision are required as the purpose of diagnosis, it is also possible to make such a contrivance that the shape of the colloid particles is made the same, for example, those having a real sphere shape are increased or the particle diameter of the colloid particles is made even, for example, the particle diameter is concentrated to a particular particle diameter such as 40 nm, 80 nm, or 120 nm, that is, a so-called colloid having a narrow particle size distribution curve is formed.

Furthermore, in order to harmonize the color developing ability of a metal colloid, since color is different depending on the particle state of gold and aggregation thereof, it is also possible to prepare a gold nanoparticle colloid having a predetermined color by mixing colloids having specific colors in a region of visible light, for example, the red gold nanoparticle colloid and the blue gold nanoparticle colloid in an arbitrary ratio.

At the time of judgment, it is also possible to enhance the precision of judgment by devising more clear color display. For example, the procedure is to appropriately combine three primary colors of light, i.e., red (wavelength: 770 to 640 nm), green (wavelength: 570 to 490 nm), and blue (wavelength: 490 to 430 nm). All the metal nanoparticle colloids are easily available from the market as products.

Incidentally, the average particle diameter can be determined by various conventional measurement methods such as determination of an average particle diameter after measurement of the particle size distribution of a colloid by using a dynamic light scattering particle size analyzer.

The reagent composition including the labeling substance solution, the analyte dilution solution, or the like for use in the present invention preferably contains a buffer or a surfactant, particularly a nonionic surfactant.

As the buffer, there is no special limitation to it so long as it has an action (buffering action) which does not cause fatal influence even by the concentration change with the addition of sample or evaporation or dilution of the sample or by contamination with more or less of a foreign matter from the outside.

Examples of the buffer include acetate buffer solution (acetic acid+sodium acetate), phosphate buffer solution (phosphoric acid+sodium phosphate), citrate buffer solution (citric acid+sodium citrate), borate buffer solution, tris-HCl buffer solution (tris(hydroxyl methyl)aminomethane+hydrochloric acid), TE buffer solution (tris+ethylenediaminetetraacetic acid), TAE buffer solution (tris+acetic acid+ethylenediaminetetraacetic acid), TBE buffer solution (tris+boric acid+ethylenediaminetetraacetic acid) and HEPES buffer solution (2-[4-(2-hydroxyl ethyl)-1-piperazinyl]ethane sulfonic acid). Preferred are HEPES buffer solution, phosphate buffer solution, acetate buffer solution, and tris-HCl buffer solution, and more preferred is HEPES buffer solution. Moreover, within the range where an adverse effect is not exerted, the other buffers may be blended and used.

Examples of the nonionic surfactant include polyoxyethylene alkyl ether, polyoxyethylene/polyoxypropylene alkyl ether (trade name: Nonion (trademark) MN811 manufactured by NOF Corporation, trade name: NP-40 manufactured by Nakarai Tesque, Inc.), polyoxyethylene sorbitan fatty acid ester (trade name "Tween" series), polyoxyethylene p-t-octyl phenyl ether (trade name "Triton" series), polyoxyethylene p-t-nonylphenyl ether (trade name "TritonN" series), alkyl polyglucoside, fatty acid diethanol amide, and alkyl monoglyceryl ether. The nonionic surfactants may be used singly or as a mixture of two or more thereof.

It is permissible for the reagent composition for use in the present invention to contain additive(s) which are known to suppress a side reaction based on biological affinity and/or a nonspecific reaction. Examples of the additives include proteins (e.g., bovine serum albumin, gelatin, etc.), high molecular compounds (e.g., polyethylene glycol, methyl cellulose, polyvinylpyrrolidone, polyvinyl alcohol, dextran, etc.), ionic surfactants or polyanions (e.g., dextran sulfate, heparin, polystyrenesulfonic acid, chondroitin sulfate, etc.), and an antimicrobial agent for promoting an antigen-antibody reaction or suppressing nonspecific reactions. They may be used with adding one or more thereof.

Moreover, it is also possible and effective and not prohibited to retain one or more of the proteins, the high molecular compounds, the ionic surfactants or the polyanions, or the antimicrobial agent for promoting the antigen-antibody reaction or suppressing nonspecific reactions, on a migration pathway of the mobile phase on the chromatography medium constituting the immobile phase.

At the time of retaining the labeling substance solution in an immobile phase, a protective stabilizing substance or a dissolution promoting substance may be contained in the labeling substance solution. Examples of the protective stabilizing substance or the dissolution promoting substance include saccharides, i.e., monosaccharides, disaccharide, trisaccharides, oligosaccharides, and polysaccharides. Examples of the monosaccharides include glucose, galactose, xylose, fructose, and the like. Examples of the disaccharides include trehalose, sucrose, lactose, maltose, and the like. Examples of the trisaccharides and oligosaccharides include raffinose and the like. Examples of the polysaccharides include gluconic acid, dextran, and the like. They may be used singly or as a mixture of two or more thereof.

Moreover, in the present invention, for providing the labeling substance retaining part in a region of the immunochromatography device, specifically, a composition containing a reagent for protecting and stabilizing the labeling substance (labeling substance protecting and stabilizing reagent-containing composition) is prepared by mixing a solution in which the labeling substance is subjected to a protection treatment with the polyalkylene glycol having a molecular weight of 1,000 to 30,000 and having one or more mercapto groups and/or a derivative thereof (protecting reagent) and arginine and casein (stabilizing reagent) and the composition is applied, adsorbed, or penetrated in the region between an end part of the sample addition part and the judgment part and then dried, whereby the labeling substance can be supported, retained, or formed at the labeling substance retaining part.

At the preparation of the labeling substance protecting and stabilizing reagent-containing composition, with regard to the order of addition of the reagents to be mixed with the labeling substance solution subjected to the protection treatment, which stabilizing reagent is mixed first or which stabilizing reagent is mixed finally may be arbitrarily determined in consideration of the state of the labeling substance protecting and stabilizing reagent-containing composition and falls within the range of design items.

For example, the polyethylene glycol having a molecular weight of 1,000 to 30,000 and having one or more mercapto groups and/or a derivative thereof may be first added to the labeling substance and then arginine or casein may be sequentially added thereto one by one.

Alternatively, the polyethylene glycol and/or a derivative thereof may be first added to the labeling substance and then a mixture of both of arginine and casein may be added thereto. Otherwise, a solution obtained by adding the polyethylene glycol derivative to the labeling substance may be added to a mixture solution of both of arginine and casein (added in random order).

At the addition, addition may be performed continuously little by little or intermittently or may be performed all at once so far as homogeneous addition is achieved, which may be appropriately performed depending on the addition amount and falls within the range of design items. Size (width) of the labeling substance retaining part, concentration, and the like may be arbitrarily determined in consideration of the performance and fall within the range of design items.

As a method for providing a site containing the labeling substance solution or the other reagent composition for use in the present invention on the immunochromatography device, for example, there may be mentioned a method of applying or penetrating the labeling substance solution for immunochromatography in a glass fiber pad (labeling substance retaining member) in the immunochromatography device and then drying the solution (e.g., through-flow drying, vacuum drying, air drying, and freeze drying) to thereby support or retain it in the glass fiber pad.

The analyte dilution solution for use in the present invention is one capable of being also used as a developing solution or a sample diluted solution. As the sample diluted solution, water is usually used as a solvent, and thereto are added a buffer solution, a salt, and a nonionic surfactant and furthermore one or two or more of proteins, high molecular compounds (e.g., PVP etc.), ionic surfactants or polyanions, antimicrobial agents, chelating agents, and the like for promoting an antigen-antibody reaction or suppressing nonspecific reactions. The addition order is not particularly limited and they may be added at the same time.

In the case of using the analyte dilution solution as the developing solution, it is possible to cause the development by supplying and dripping on the sample pad (sample addition part) a mixture preliminarily prepared of the detection sample and the developing solution, or it is possible to cause the development first by supplying and dripping the sample on the sample pad (sample addition part) and then by supplying and dripping the developing solution on the sample pad (sample addition part).

In the case of using the analyte dilution solution as the sample dilution solution, the dilution solution that adjusts or dilutes the analyte to a concentration suitable for measurement may be used as the development solution, as it is, by supplying and dripping the dilution solution on the sample pad (sample addition part).

Major examples of the analyte (sample containing the detection target) in the present invention include biological samples, i.e., blood, serum, blood plasma, urine, saliva, cerebrospinal fluid, sweat, tear, amniotic fluid, nipple discharge, nasal discharge, phlegm, a swab from nasal cavity or pharynx, exudates from skin, tissue, cells, and an extract from feces.

The detection target in the present invention may be one for which a substance specifically binding to it, for example, specifically binding as in an antigen-antibody reaction is present or can be prepared, and is not particularly limited. The detection target may be one that itself has immunogenicity, like complete antigen, or it may be one that itself does not have immunogenicity itself, like hapten (incomplete antigen) but has an ability to acquire immunogenicity through a chemical modification. Any one for which a substance that specifically combines with any of such detection target is present or can be prepared may be sufficient and may be made a monoclonal antibody or a polyclonal antibody.

Examples of the detection target in the present invention include peptide hormones (growth hormone (GH), adrenocorticotropic hormone (ACTH), melanocyte stimulating hormone (MSH), prolactin, thyroid stimulating hormone (TSH), luteinizing hormone (LH), follicle stimulating hormone (FSH), pituitary hormone, calcium metabolism regulating hormone, pancreatic hormone, gut hormone, vasoactive hormone, placental hormone such as human chorionic gonadotropic hormone (hCG)), follicle hormone such as estrone, natural or synthetic corpus luteum hormone such as progesterone, male hormone such as testosterone, adrenocortical hormone such as cortisol, thyroid hormone such as diiodothyronine, prostatic acid phosphatase (PAP), prostate specific antigen (PSA), alkali phosphatase, transaminase, trypsin, pepsinogen, α-fetoprotein (AFP), tumor specific substances such as carcinoembryonic antigen (CEA), serum protein components such as immunoglobulin G (IgG), rheumatism factors, serotonin, Urokinase, ferritin, substance P, fecal occult blood, syphilitic antibody, influenza virus, adenovirus, rotavirus, mycoplasma, HBs antigen, HBs antibody, chlamydial antigen, group A β hemolytic streptococcus antigen, other steroids such as cholesterol, bile acid, cardiotonic steroid, and sapogenin, epinephrine, dopamine, physiologically active alkaloids, amino group-containing psychotropic agents, low molecular weight peptides such as TRH, prostaglandins, vitamins, antibiotics such as penicillin, other in-vivo components, drugs to be administered in vivo, and metabolites thereof.

Of these, pathogens such as viruses or bacteria are preferred and, more preferred are influenza virus, adenovirus, rotavirus, and mycoplasma. In this case, examples of the analyte (sample containing a detection target) include nasal discharge, phlegm, and a swab from nasal cavity or pharynx.

In the case where a swab from pharynx is used as the analyte, after the swab from pharynx is diluted using the analyte dilution solution, it is supplied and dripped on the sample pad in the immunochromatography device. The test kit for immunochromatography of the present invention is effective for a test for the presence of a pathogen and particularly, prompt and precise curative measures can be taken based on the results of the test for the presence of a specific virus.

The structure and operation and detection method of the immunochromatography device for testing the presence of a virus or the like existing in a biological sample such as nasal discharge, phlegm, and a swab from nasal cavity or pharynx are known.

Tests such as identification and quantitative determination of a detection target in a sample, e.g., influenza virus in a swab from pharynx, can be conducted by supplying/dripping the analyte dilution solution of the present invention containing a biological sample (analyte), into a sample pad of a conventional immunochromatography device and performing a specifically binding reaction such as an antigen-antibody reaction using an immunochromatography device on which the labeling substance solution of the present invention is supported, for example, by drying the solution after impregnation.

Figure 1:
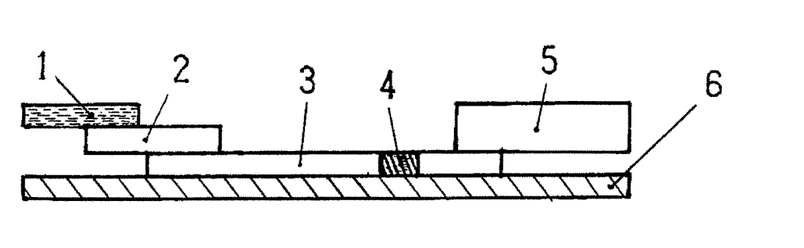
FIG. 1 is a schematic drawing of a test piece for an immunochromatography device.

The immunochromatography device and specification thereof will hereinafter be described. The immunochromatography device is comprised of (1) a sample addition part (1) (sample pad), a labeling substance retaining part (2), a chromatography medium part (3), a detection part (4), an absorption part (5), and a backing sheet (6). The structures, specifications, and embodiments of individual parts thereof are as follows.

1) The sample addition part (1) (sample pad) is comprised of a porous sheet, which has a characteristic such that it absorbs a sample promptly but can retain it so weakly that the sample migrates to the reaction part speedily, with reference to FIG. 1. Examples of the porous sheet include cellulose filter paper, glass fiber filter paper, polyurethane, polyacetate, cellulose acetate, nylon, and cotton. Of these, glass fiber filter paper is preferred.

In the present invention, in order to suppress the nonspecific reactions, it is possible to adopt an embodiment wherein the reagent composition for immunochromatography containing a buffer solution, a nonionic surfactant and the like is supported by a method of penetrating it into the sample addition part (1) beforehand, and then drying it. For example, it is possible and effective, with no obstruction, to adopt an embodiment wherein any of the components of the reagent composition for immunochromatography, containing components of tris-HCl buffer solution and polyoxyethylene/polyoxypropylene block copolymer having an alkyl group at one end, is supported or retained beforehand.

2) In the labeling substance retaining part (2), a labeling reagent, in which a reagent component is labeled with a labeling component, is supported or retained. As the labeling component, there can be used metal colloidal particles such as gold colloidal particles and silver colloidal particles, colored latex particles obtained through dyeing of a synthetic high polymer synthesized by (co-)polymerization of various monomers, enzymes, fluorescent compounds, or the like. The reagent component is a particle or a molecule capable of recognizing a substance to be analyzed, and preferably it is a monoclonal antibody or a polyclonal antibody or their fragments (a second reagent).

3) The chromatography medium part (3) consists of a film carrier and a judgment site (4) formed on the film carrier. The film carrier is not particularly limited so long as it can absorb a sample analyte by means of capillary phenomenon and can migrate the analyte. For example, the carrier may be selected from the groups consisting of cellulose nitrate, cellulose acetate, nylon, polyether sulfone, polyvinyl alcohol, polyester, glass fiber, polyolefin, cellulose, and a synthetic polymer made of mixed fibers thereof. The carrier consists of any one of fibers, woven fabrics, non-woven fabrics, fabrics, films, and the like thereof.

4) In the detection part (4), a monoclonal antibody or a polyclonal antibody or their fragments (a first reagent) is supported and fixed on a sheet of cellulose nitrate. One or both of the reagent component (the first reagent) for use in the judgment part (4) and the reagent component (the second reagent) for use in the labeling reagent may be a monoclonal antibody or a polyclonal antibody, but it is preferable that at least one of them is a polyclonal antibody if the manufacturing cost and the stable supply of the antibody are considered with maintaining the specificity. Furthermore, the reagent component (the second reagent) for use in the labeling reagent is more preferably a monoclonal antibody having high specificity from the viewpoint of measurement sensitivity and the like. In the test for an analyte having high pathogenicity such as influenza virus, it is most preferable that both of them are monoclonal antibodies.

Monoclonal antibodies and polyclonal antibodies and their fragments are known and available, and are able to be prepared by known methods. Examples of antibody-producing animal species include human, mouse, rat, rabbit, and goat. The immunoglobulin may be any of IgG, IgM, IgA, IgE, and IgD.

The monoclonal antibody is obtained by hybridizing mouse's spleen cell which has been immunized by an antigen (e.g., influenza virus etc.) with its myeloma cell, selecting a hybridoma which produces an aimed antibody, and obtaining the monoclonal antibody produced by the hybridoma, according to usual methods. For example, please refer to the Köhler and Milstein technique (Nature 256 (1975) p. 495-497).

The polyclonal antibody can be obtained in a usual manner by isolating an objective antibody from an antiserum obtained by immunizing a producing animal (e.g., human, mouse, rat, rabbit, goat, or horse) with an antigen (influenza virus etc.).

Influenza viruses are classified into A type, B type, and C type based on difference in antigenicity of M1 protein (which is localized inside the envelop in such a manner that the protein lines the envelop and plays a role of a substantial shell) and NP protein (which exists inside the envelop, spirally winds on the nucleoprotein, and corresponds a nucleocapsid) among proteins constituting the virion.

An A type influenza virus exhibiting large epidemic scale and large damage at infection is a minus-chain single-strand RNA virus having a diameter of about 80 to 120 nm and having an envelop (shell) and, based on difference in antigenicity of hemagglutinin (HA) and neuraminidase (NA) that are virus surface proteins, the A type viruses are further classified into subtypes of 16 kinds in terms of HA (H1 to H16) and 9 kinds in terms of NA (N1 to N9).

As the reagent component for use in the detection part (4) (first reagent) and the reagent component for use in the labeling reagent (second reagent), it is possible to use either anti-influenza virus monoclonal antibody or anti-influenza virus polyclonal antibody. However, it is most preferable to use the anti-influenza virus monoclonal antibody as both reagents from the viewpoints of precision and efficiency of the reaction.

5) In the absorption part (5), a material capable of promptly absorbing an excess of the sample, glass filtration paper or the like is used.

6) The backing sheet (6) is a base material. By applying an adhesive agent or an adhesive tape to one side of it, that side is made adhesive, and onto this adhesive side, part or all of the sample addition part (1), the labeling material retaining part (2), the chromatography medium part (3), the detection part (4), and the absorption part (5) are provided with close adhesion. With regard to the backing sheet (6), the base material is not particularly limited so long as the material is made impermeable to the sample liquid and impermeable to moisture by an adhesive agent.

The following will outline the principle of the judgment using the case where the detection target is an influenza virus as a specific example:

1. A sample (e.g., an analyte such as a swab from pharynx) is prepared or diluted with an analyte dilution solution to such a concentration that the sample migrates smoothly in the immunochromatography medium without lowering the measurement precision, thereby forming an analyte sample (analyte dilution solution containing the analyte). A predetermined amount (normally 0.1 to 2 ml) of the analyte sample is dripped onto the sample addition part (1). When the analyte sample is dripped, the analyte sample begins to migrate in the sample addition part (1).

2. Then, the analyte sample migrates to the labeling material retaining part (2). As the time when the analyte sample passes through this part, a dissolution assisting substance retained at the labeling material retaining part (2) is first dissolved in the moisture of the analyte sample and then the protective stabilizing substance retained together with the labeling substance and the labeling substance are dissolved in the moisture of the analyte sample and migrate with the analyte sample.

3. Then, the labeling reagent dissolved in the moisture of the analyte sample passes through the detection part (4) on the chromatography medium part (3). Here, the nonspecific reactions are suppressed by the reagent composition for immunochromatography containing the protective stabilizing substance and the like dissolved in the analyte sample, and by virtue of the specific binding reaction between the antigen and the antibody, in the case where an influenza virus is present, the influenza virus in the analyte sample undergoes a specific reaction to bind to the antibody, which is retained, i.e., supported and fixed at the detection part (4), and the labeling reagent in such a manner that the virus is sandwiched between the antibody and the labeling reagent, whereby the detection part (4) is colored. In the case where an influenza virus is absent, the labeling reagent dissolved in the moisture of the sample does not trigger a specific reaction even when it passes through the detection part (4) on the chromatography medium part (3), so that the detection part (4) is not colored.

4. In the end, the moisture of the sample migrates toward the absorption part (5). In this manner, for example, by testing the presence of an influenza virus in the analyte sample, it is possible to judge the presence of infection with the influenza virus with precision.

Nasal discharge, phlegm, or a swab from nasal cavity or pharynx that is a collected sample can be subjected to the test similar to the above by diluting them to about 10 to 100 times with a sample dilution solution, and dripping/supplying 150 μL of it onto the sample addition part (1), followed by developing, and thereby it is possible to attain similar results as mentioned above.

The following will explain the effectiveness of the present invention with reference to examples and embodiments according to individual specifications, but the present invention should not be construed as being limited thereto.

EXAMPLES

The following will explain the significance of the present invention with reference to Examples and Comparative Examples. The specifications carrying out the same are as follows.

Example 1

(1) Preparation of Judgment Part on Chromatography Medium

As a membrane, a sheet (manufactured by Millipore, trade name: HF 12250 mm×25 mm) made of nitrocellulose was used. An anti-influenza A type virus monoclonal antibody (first antibody) was diluted with a 10 mM phosphate buffer solution (pH 7.4) containing 5% by mass sucrose and 5% by mass isopropanol so as to give the concentration of 1.0 mg/ml. The diluted solution (150 μL) was applied on the membrane with the width of 1 mm by means of an antibody applicator (manufactured by BioDot Company), followed by drying at 50° C. for 30 minutes and then dried at room temperature overnight to prepare a judgment part on the chromatography medium.

(2) Preparation of Labeling Substance Solution

An anti-influenza A monoclonal antibody (0.1 mL) diluted with HEPES buffer (pH 7.5) so as to give the concentration of 0.1 mg/mL was added to 0.5 mL of a gold colloidal suspension (manufactured by Tanaka Kikinzoku Kogyo, average particle diameter: 40 nm), followed by allowing to stand at room temperature for 10 minutes. Then, 0.1 ml of HEPES buffer solution (pH 7.5) containing 0.01% by mass PEG-SH (manufactured by NOF Corporation, trade name: SUNBRIGHT ME-050SH, molecular weight: 5,000) was added (PEG-SH concentration after addition: 0.001% by mass), followed by allowing to stand at room temperature for 10 minutes. After thorough stirring, centrifugation was carried out for 15 minutes at 8000×g. After removal of the supernatant, 0.1 mL of a phosphate buffer (pH 7.4) containing 1% by mass bovine serum albumin was added, thereby preparing a labeling substance solution.

(3) Preparation of Test Piece for Immunochromatography

To a 200 μL of the labeling substance solution prepared above were added a phosphate buffer solution (pH 9.0) containing 100 μL of a 25% by mass aqueous trehalose solution and 80 μL of 5% by mass casein (final concentration: 1% by mass) and 5 μl of a 10% by mass aqueous L-arginine solution (final concentration: 0.1% by mass). The resulting mixture was added to a 12 mm×100 mm glass fiber pad (manufactured by Millipore) so as to be uniform and then dried in a vacuum drier to prepare a labeling substance retaining member. Next, the chromatographic medium having the judgment part prepared above, the labeling substance retaining member, a sample pad made of glass fiber to be used as a portion to which a sample is added, and an absorption pad for absorbing a developed sample or labeling substance were attached to a base material made of a backing sheet. The resulting laminate was cut into a 5-mm wide piece by a cutter and the piece was used as a test piece for immunochromatography.

(4) Preparation of Analyte Dilution Solution

A 50 mM HEPES buffer solution (pH 7.5) containing 1% by mass nonionic surfactant (a 1:1 mixture of trade name: MN811 manufactured by NOF Corporation and trade name: NP-40 manufactured by Nakarai Tesque), 80 mM potassium chloride, 20 mM guanidine hydrochloride, and 0.4% by mass polyvinylpyrrolidone (average molecular weight: 360,000) was prepared and was used as a reagent for a dilution treatment of an analyte such as nasal discharge, phlegm, or a swab from pharynx.

(5) Measurement

The presence of influenza A type virus as an antigen in an analyte was measured according to the following method by using the test piece for immunochromatography and the analyte dilution solution prepared above. Namely, a nasal discharge was collected by inserting one end of the tube of a suction trap in a suction pump and the other end of the tube in the inner part of the nasal cavity of a person who was not infected with influenza and setting the suction pump at negative pressure.

The nasal discharge thus collected was diluted 20 times with the analyte dilution solution and the diluted one was used as a negative analyte sample. A positive analyte sample was prepared by adding a commercially-available inactivated influenza A type virus antigen to the negative analyte sample so as to give the protein concentration of 25 ng/mL.

The negative analyte sample and the positive analyte sample, each 120 μL, were added and developed on the sample pad of the test piece for immunochromatography and 15 minutes later, visual judgment was conducted. When a red line of the test line was confirmed, the sample was judged as "+"; when a red test line was clearly confirmed, the sample was judged as "++"; when a red test line was more clearly confirmed, the sample was judged as "+++"; when a red line was confirmed but it was a very pale one, the sample was judged as "±"; and when no red line was confirmed, the sample was judged as "−". The results are shown in Table 1.

Example 2

The measurement was conducted in the same manner as in Example 1 except that 0.01% by mass PEG-SH (molecular weight: 2,000) was used as a protective agent for the labeling substance in the step of (2) Preparation of Labeling substance Solution in Example 1. Judgment was conducted according to the same visual judgment criteria. The results of the judgment are shown in Table 1.

Example 3

The measurement was conducted in the same manner as in Example 1 except that 0.01% by mass PEG-SH (molecular weight: 20,000) was used as a protective agent for the labeling substance in the step of (2) Preparation of Labeling substance Solution in Example 1. Judgment was conducted according to the same visual judgment criteria. The results of the judgment are shown in Table 1.

Comparative Example 1

The measurement was conducted in the same manner as in Example 1 except that 0.01% by mass PEG (molecular weight: 20,000), i.e., polyethylene glycol having no mercapto group, was used as a protective agent for the labeling substance in the step of (2) Preparation of Labeling substance Solution in Example 1. Judgment was conducted according to the same visual judgment criteria. The results of the judgment are shown in Table 1.

Comparative Example 2

Measurement was conducted in the same manner as in Example 1 except that polyvinylpyrrolidone (PVP K-90, molecular weight: 630,000) expected to have the same function was used as a protective agent for the labeling substance instead of 0.01% by mass PEG (molecular weight: 5,000) in the step of (2) Preparation of Labeling substance Solution in Example 1. Judgment was conducted according to the same visual judgment criteria. The results of the judgment are shown in Table 1.

Comparative Example 3

Measurement was conducted in the same manner as in Example 1 except that 0.01% by mass PEG-SH (molecular weight: 5,000) was used as a protective agent for the labeling substance in the step of (2) Preparation of Labeling substance Solution in Example 1 and "L-glutamic acid" was used as an amino acid component of the labeling substance retaining part instead of L-arginine. Judgment was conducted according to the same visual judgment criteria. The results of the judgment are shown in Table 1.

Comparative Example 4

Measurement was conducted in the same manner as in Example 1 except that 0.01% by mass PEG-SH (molecular weight: 5,000) was used as a protective agent for the labeling substance in the step of (2) Preparation of Labeling substance Solution in Example 1 and "L-glutamic acid+guanidine hydrochloride" was used as an amino acid component of the labeling substance retaining part instead of L-arginine. Judgment was conducted according to the same visual judgment criteria. The results of the judgment are shown in Table 1.

Comparative Example 5

Measurement was conducted in the same manner as in Example 1 except that a HEPES buffer solution (pH 7.5) containing PEG-SH (manufactured by NOF Corporation, trade name: SUNBRIGHT ME-050SH, molecular weight: 5,000) was used as a protective agent for the labeling substance in the step of (2) Preparation of Labeling substance Solution in Example 1, L-arginine was used as an amino acid component of the labeling substance retaining part, and "BSA" was used instead of casein that is a protein component of the labeling substance retaining part. Judgment was conducted according to the same visual judgment criteria. The results of the judgment are shown in Table 1.

TABLE 1

| | Protective agent for labeling substance | Amino acid component of labeling substance retaining part | Protein component of labeling substance retaining part | Visual judgment after 15 minutes of development Antigen level | | |
|---|---|---|---|---|---|---|
| | | | | 0 ng | 25 ng | 50 ng |
| Example 1 | PEG-SH (molecular weight 5000) | L-arginine | casein | − | ++ | +++ |
| Example 2 | PEG-SH (molecular weight 2000) | L-arginine | casein | − | + | ++ |
| Example 3 | PEG-SH (molecular weight 20000) | L-arginine | casein | − | + | ++ |
| Comparative Example 1 | PEG (molecular weight 20000) | L-arginine | casein | + | + | ++ |
| Comparative Example 2 | PVP K-90 (molecular weight 630000) | L-arginine | casein | ± | + | ++ |
| Comparative Example 3 | PEG-SH (molecular weight 5000) | L-glutamic acid | casein | + | + | ++ |
| Comparative Example 4 | PEG-SH (molecular weight 5000) | L-glutamic acid + guanidine hydrochloride | casein | + | + | ++ |
| Comparative Example 5 | PEG-SH (molecular weight 5000) | L-arginine | BSA | ± | ± | + |

5. Estimation of Effects Attributable to Components to be Blended

1) From the results of Examples 1 to 3 in Table 1, it is realized that positive or false positive such as "+" or "±" is not shown at an antigen level of 0 ng and thus the blank coloring and the nonspecific reactions are suppressed only in the cases where a HEPES buffer solution (pH 7.5) containing PEG-SH (molecular weight: 2,000 to 20,000) is used as a protective agent for the labeling substance and a phosphate buffer solution (pH 9.0) containing casein and an aqueous L-arginine solution are blended thereto.

2) As shown in "Comparative Example 1" and "Comparative Example 2", it is realized that positive or false positive such as "+" or "±" is shown at an antigen level of 0 ng and thus precise test results are not obtained even when casein is used as a protein component of the labeling substance retaining part and L-arginine is used as an amino acid component of the labeling substance retaining part, in the cases where PEG-SH (manufactured by NOF Corporation, trade name: SUNBRIGHT ME-050SH, molecular weight: 5,000) is not used and PEG (molecular weight: 20,000) or PVP K-90 (molecular weight: 630,000) is used as a protective agent for the labeling substance (i.e., in the cases of Comparative Examples 1 and 2).

3) As shown in Comparative Examples 3 and 4, it is realized that positive such as "+" is shown at an antigen level of 0 ng and thus the blank coloring or the nonspecific reactions are induced even when a HEPES buffer solution (pH 7.5) containing PEG-SH (manufactured by NOF Corporation, trade name: SUNBRIGHT ME-050SH, molecular weight: 5,000) is used as a protective agent for the labeling substance and a phosphate buffer solution (pH 9.0) containing casein is used thereto, in the cases where L-arginine is not used and L-glutamic acid or a mixture of L-glutamic acid and guanidine hydrochloride is used as an amino acid component of the labeling substance retaining part (i.e., in the cases of Comparative Examples 3 and 4).

4) As shown in "Comparative Example 5", it is realized that false positive such as "±" is shown at antigen levels of 0 ng and 25 ng and thus precise test results are not obtained even when a HEPES buffer solution (pH 7.5) containing PEG-SH (manufactured by NOF Corporation, trade name: SUNBRIGHT ME-050SH, molecular weight: 5,000) is used as a protective agent for the labeling substance and L-arginine is used as an amino acid component of the labeling substance retaining part, in the cases where casein is not used and BSA is used as a protein component of the labeling substance retaining part (i.e., in the cases of Comparative Example 5).

The following will explain in detail the fact that significance can be confirmed by performing the present invention in accordance with the above Examples 1 to 3 in the case of performing the present invention but it can be similarly confirmed even in the case where the present invention is performed with slightly changing the conditions of Examples, by giving Test Examples or Embodiments. However, the present invention should not be construed as being limited to these Test Examples and Embodiments.

Embodiment 1

As another embodiment, measurement was conducted in the same manner using a mixture of PEG-SH (manufactured by NOF Corporation, trade name: SUNBRIGHT ME-050SH, molecular weight: 5,000) and PEG-SH (manufactured by NOF Corporation, trade name: SUNBRIGHT ME-020SH, molecular weight: 2,000) instead of PEG-SH (manufactured by NOF Corporation, trade name: SUNBRIGHT ME-050SH, molecular weight: 5,000) that is a protective agent for the labeling substance in the above Example 1. It is possible to achieve about the same purpose as in the case of PEG-SH (manufactured by NOF Corporation, trade name: SUNBRIGHT ME-050SH, molecular weight: 5,000) alone in the above Example 1.

Embodiment 2

Moreover, measurement was conducted in the same manner using, instead of PEG-SH (manufactured by NOF Corporation, trade name: SUNBRIGHT ME-200SH, molecular weight: 20,000) in the above Example 3, a mixture of the same and PEG-SH (manufactured by NOF Corporation, trade name: SUNBRIGHT ME-050SH, molecular weight: 5,000). It can be confirmed that it is possible to achieve about the same purpose as in the case of PEG-SH (molecular weight: 20,000) alone in the above Example 3.

Embodiment 3

Furthermore, measurement was conducted in the same manner using PEG-SH (manufactured by NOF Corporation, trade name: SUNBRIGHT ME-100SH, molecular weight: 10,000) instead of PEG-SH (manufactured by NOF Corporation, trade name: SUNBRIGHT ME-050SH, molecular weight: 5,000), as a protective agent for the labeling substance in the above Example 1. It can be confirmed that it is possible to achieve about the same purpose as in the case of the above Test Example 1.

Embodiment 4

Next, there are shown specifications of concentration of a polyethylene glycol derivative having one or more mercapto groups which is a protective group in a solution in which a labeling substance is subjected to a protection treatment with the protective agent and final concentration of two components of arginine as an amino acid component and casein as a protein component to be mixed into the solution subjected to the protection treatment (Table 2).

Measurement is conducted in the same manner as in Example 1 except that the labeling substance was subjected to the protection treatment with controlling the solution concentration (% by mass) of the polyethylene glycol derivative (A) having one or more mercapto groups after the protection treatment to a concentration of 0.0005, 0.005, 0.01, or 0.001% by mass.

Measurement is conducted in the same manner as in Example 1 except that the final concentration (% by mass) of the arginine solution (B) is controlled to a concentration of 0.5, 0.2, 0.02, 0, or 0.1% by mass.

Measurement is conducted in the same manner as in Example 1 except that the final concentration (% by mass) of the casein solution (C) is controlled to a concentration of 0.2, 5, 2, 1, or 0% by mass.

(Incidentally, calculated according to: weight part of each component=concentration of each component×blending amount of each component×100)

TABLE 2

| Embodiment (formulation example) | 1 | 2 | 3 | 4 | 5 |
|---|---|---|---|---|---|
| A (% by mass) | 0.0005 | 0.005 | 0.01 | 0.001 | 0.001 |
| B (% by mass) | 0.5 | 0.2 | 00.2 | 0 | 0.1 |
| C (% by mass) | 0.2 | 5 | 2 | 1 | 0 |

Even in the cases of using a solution having a composition ratio of three components as in the above Embodiments (Formulation Examples) 1 to 3, it is stable in change with time, further the color of the labeling substance is very clear, measurement time, handling, and measurement precision are improved, and about the same degree of judgment results as in Example 1 are achieved.

Moreover, in the case where arginine as an amino acid component is not contained as in the case of the above Embodiment (Formulation Example) 4, positive is shown even at an antigen level of 0 ng and not only blank coloring or a nonspecific reaction is induced but also part of the labeling particles are aggregated at the time of development and decrease in sensitivity and/or uneven development take place. Furthermore, also in the case where casein as a protein component is not contained as in the case of the above Embodiment (Formulation Example) 5, false positive is shown even at an antigen level of 0 ng and not only a nonspecific reaction is induced and precise test results are not obtained but also part of the labeling particles are aggregated at the time of development and decrease in sensitivity or uneven development takes place.

Next, specifications of concentration of guanidine hydrochloride in the analyte dilution solution in Example 1 are shown as Examples 5 to 9.

Examples 5 to 9

Measurement was conducted in the same manner as in Example 1 except that the concentration of guanidine hydrochloride in the analyte treatment solution in each example of Examples 5 to 9 is controlled to 2, 5, 20, 50, or 100 mM, and repeated experiments were conducted three times for each measurement. Specifications and results thereof are shown in Table 3.

TABLE 3

| | Concentration of guanidine hydrochloride | Visual judgment after 15 minutes of development Antigen level | | |
|---|---|---|---|---|
| | (mM) | 0 ng | 25 ng | 50 ng |
| Example 5 | 2 | − | ++ | +++ |
| | | − | ++ | +++ |
| | | ± | ++ | +++ |
| Example 6 | 5 | − | ++ | +++ |
| | | − | ++ | +++ |
| | | − | ++ | +++ |
| Example 7 | 50 | − | + | ++ |
| | | − | ++ | +++ |
| | | − | ++ | +++ |
| Example 8 | 100 | − | + | ++ |
| | | − | ± | + |
| | | − | ± | + |

As above, it was found that the presence of a pathogen can be tested with good sensitivity and precision with suppressing blank coloring and nonspecific reactions by using a combination of a polyethylene glycol derivative having one or more mercapto groups as a protective agent for the labeling substance, L-arginine as an amino acid component of the labeling substance retaining part, and casein as a protein component of the labeling substance retaining part.

While the present invention is described in detail and with referring to specific embodiments, it is apparent for those skilled in the art that various changes and modifications can be given without departing from the spirit and scope of the present invention. The present application is based on Japanese Patent Application (Japanese Patent Application No. 2012-066409) filed on Mar. 22, 2012 and the content of which is incorporated herein by reference.

INDUSTRIAL APPLICABILITY

The detection kit of the present invention is capable of suppressing blank coloring and nonspecific reactions and capable of specifically detecting the presence of a pathogen in nasal discharge, a swab from nasal cavity, a swab from pharynx, or phlegm at high sensitivity and with precision, so that it enables prompt treatment of diseases, and thus the kit has industrial applicability.

DESCRIPTION OF REFERENCE NUMERALS AND SIGNS

1: sample addition part (sample pad)
2: labeling substance retaining part
3: chromatography medium part
4: detection part
5: absorption part
6: backing sheet

The invention claimed is:

1. An immunochromatography detection method comprising:
a step of adding an analyte dilution solution containing an analyte into a sample addition part;
a step of recognizing a detection target by a labeling substance modified with gold nanoparticles, which is dry-retained at a labeling substance retaining part;
a step of developing a composite of the labeling substance and the detection target as a mobile phase; and
a step of detecting the detection target in the developed mobile phase at a detection part,
wherein the labeling substance is protected with polyethylene glycol having one or more mercapto groups and/or a derivative of the polyethylene glycol having one or more mercapto groups, the polyethylene glycol having one or more mercapto groups and/or the derivative of the polyethylene glycol having one or more mercapto groups, having a molecular weight of 1,000 to 30,000, wherein the concentration of the polyethylene glycol having one or more mercapto groups and/or the derivative of the polyethylene glycol having one or more mercapto groups in the labeling substance solution is from 0.0001 to 0.05% by mass, and wherein the protected labeling substance solution is subsequently dry-retained together with arginine and casein at the labeling substance retaining part.

2. The immunochromatography detection method according to claim 1, wherein the above arginine and casein are dry-retained at the labeling substance retaining part with being contained in the labeling substance solution and impregnating the chromatography medium and, as a final concentration in the labeling substance solution before being moistened with the chromatography medium, concentration of arginine is from 0.01 to 2% by mass and concentration of casein is from 0.1 to 10% by mass.

3. The immunochromatography detection method according to claim 1, wherein the gold nanoparticles are red gold nanoparticles having an average particle diameter of 30 to 100 nm or blue gold nanoparticles having an average particle diameter of 20 to 200 nm.

4. The immunochromatography detection method according to claim 1, wherein the analyte is nasal discharge, a swab from nasal cavity, a swab from pharynx, or phlegm.

5. The immunochromatography detection method according to claim 1, wherein guanidine is contained in the analyte dilution solution.

6. The immunochromatography detection method according to claim 5, wherein concentration of guanidine in the analyte dilution solution is from 1 to 200 mM.

7. An immunochromatography device comprised substantially and sequentially of a sample addition part, a labeling substance retaining part, a chromatography medium part, a detection part and an absorption part, wherein the labeling substance retaining part is provided between an edge part of the sample addition part and the detection part, and the labeling substance retaining part comprises a labeling substance which is protected with polyethylene glycol having one or more mercapto groups and/or a derivative of the polyethylene glycol having one or more mercapto groups, the polyethylene glycol having one or more mercapto groups and/or the derivative of the polyethylene glycol having one or more mercapto groups, having a molecular weight of 1,000 to 30,000, wherein the concentration of the polyethylene glycol having one or more mercapto groups and/or the derivative of the polyethylene glycol having one or more mercapto groups in the labeling substance solution is from 0.0001 to 0.05% by mass, together with arginine and casein.

8. A detection kit comprising an immunochromatography device comprised substantially and sequentially of a sample addition part, a labeling substance retaining part, a chromatography medium part, a detection part and an absorption part, wherein the labeling substance retaining part is provided between an edge part of the sample addition part and the detection part, and the labeling substance retaining part comprises a labeling substance which is protected with polyethylene glycol having one or more mercapto groups and/or a derivative of the polyethylene glycol having one or more mercapto groups the polyethylene glycol having one or more mercapto groups and/or the derivative of the polyethylene glycol having one or more mercapto groups, having a molecular weight of 1,000 to 30,000, wherein the concentration of the polyethylene glycol having one or more mercapto groups and/or the derivative of the polyethylene glycol having one or more mercapto groups in the labeling substance solution is from 0.0001 to 0.05% by mass, together with arginine and casein.

* * * * *

UNITED STATES PATENT AND TRADEMARK OFFICE
CERTIFICATE OF CORRECTION

PATENT NO. : 9,863,945 B2  
APPLICATION NO. : 14/386653  
DATED : January 9, 2018  
INVENTOR(S) : Daisuke Ito Page 1 of 1

It is certified that error appears in the above-identified patent and that said Letters Patent is hereby corrected as shown below:

In the Claims

Claim 3, Column 24, Line 64 change "particle diameter of 20 to 200 run" to -- particle diameter of 20 to 200 nm --.

Claim 7, Column 25, Lines 13 and 14 change "labeling substance retaining part comprises a labeling substance" to -- labeling substance retaining part comprises arginine, casein and a labeling substance --.

Claim 7, Column 26, Line 2 delete ", together with arginine and casein.".

Claim 8, Column 26, Lines 9 and 10 change "labeling substance retaining part comprises a labeling substance" to -- labeling substance retaining part comprises arginine, casein and a labeling substance --.

Claim 8, Column 26, Line 21 delete ", together with arginine and casein.".

Signed and Sealed this  
Twenty-eighth Day of May, 2019

Andrei Iancu  
*Director of the United States Patent and Trademark Office*